United States Patent [19]

Ellison et al.

[11] Patent Number: Plant 6,967

[45] Date of Patent: Aug. 1, 1989

[54] ASPARAGUS PLANT—'LOUISE'

[75] Inventors: J. Howard Ellison, Milltown; John J. Kinelski, Princeton, both of N.J.

[73] Assignee: Rutgers University, New Brunswick, N.J.

[21] Appl. No.: 159,682

[22] Filed: Feb. 24, 1988

[51] Int. Cl.[4] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

An Asparagus plant having female characteristics which plant includes tolerance to rust (*Puccinia asparagi*) Fusarium infestation, imparting to progeny by sexual and asexual reproduction those elements together with vigor, high yield and tight spear tip formation.

1 Drawing Sheet

This invention relates to Asparagus plants and is one of the results of a program of development which has continued over many years, producing important additions to the art of cultivating and producing Asparagus, not only for commercial table use, but to provide parents for improved varieties.

The fact that improved varieties of asparagus, with increasing resistance to disease are constantly being sought by us, enables us to select plants which appear to offer probabilities of improved progeny and for that purpose we have selected female plants from time to time which will produce seed that in turn results in improved plants as well as plants which may be reproduced by asexual means.

The instant plant is an example of the female plant which was selected from our cross 14×14, Cross No. 362. The plant selected did in fact have rust (*Puccinia asparagi*), and Fusarium tolerance, as well as other aspects which we deem valuable.

Since the plant hereof is a female plant, we have chosen to call the same "Louise" and as asexually reproduced in successive generations found that the desirable tolerance to rust and Fusarium, together with vigor, high yield and tight spear tip production are transmitted to progeny.

We have caused our new plant to be asexually reproduced both by crown division and tissue culture.

We have also determined that when sexually combined with the male "Scott Howard" (U.S. Plant Pat. No. 5,549) it produces all male asparagus, one in particular which we have also selected and denominate as "Jersey General", the subject of separate application for patent.

BRIEF DESCRIPTION OF THE DRAWINGS

Since asparagus plants are not generally clearly distinct either in form or color the above data is highly desirable for identifying our new plant, the drawing appended hereto in FIG. 1 showing a part of a typical plant of our new variety with some of the data from the table applied thereto.

The color photo of FIG. 2 shows such plant in color as nearly representative thereof as it is possible to provide in a photograph of this kind with color reference where used herein applying to Munsell Limit Color Cascade of Macbeth Division of Kollmorgen Corporation.

DETAILED BOTANICAL DESCRIPTION

Figure 2:
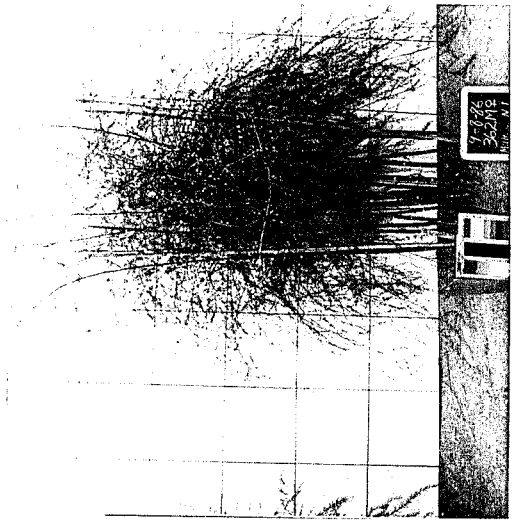
Figure 1:
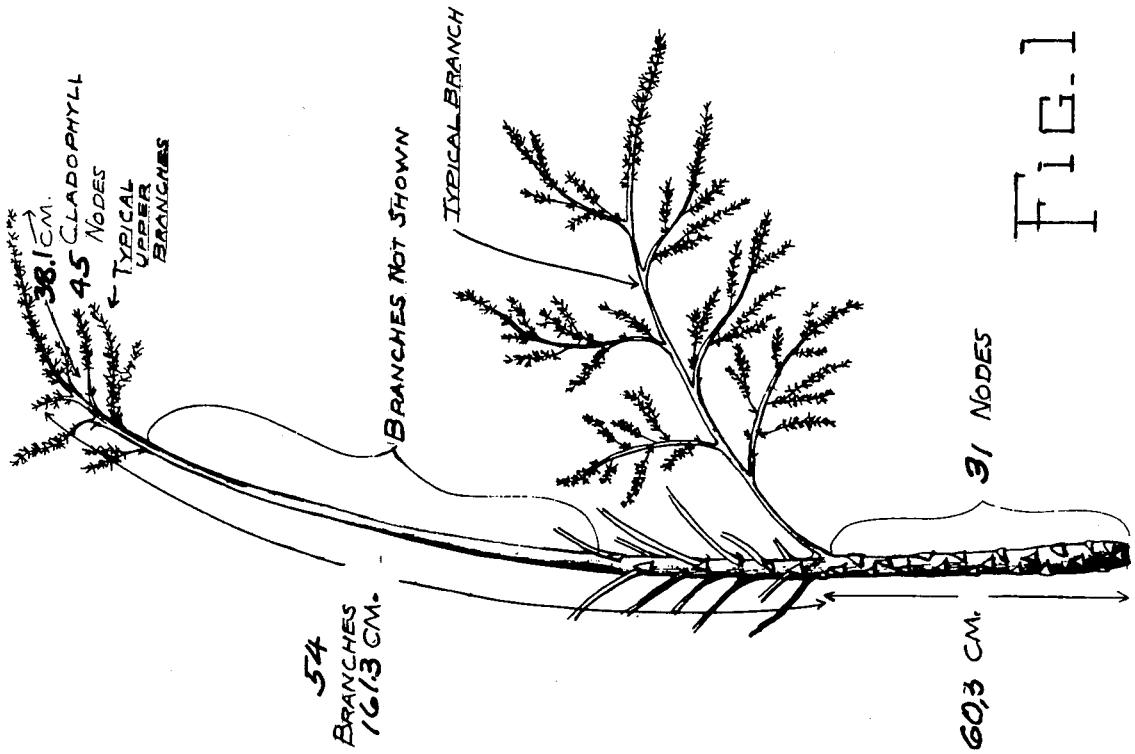

It is notable that the female plant, "Louise", has many desirable characteristics, including those referred to before and as part of our program we have assembled data to identify the same which for a typical plant is set forth below. , The dimensions to follow are presented in centimeters unless otherwise indicated. The number "1", in parenthesis, indicates that the reported measurements were taken from the largest stalk.

ASPARAGUS PLANT DATA

| Asparagus plant "Louise" (362M female) | Inch × 2.54=cm. |
|---|---|
| Stalk data | |
| Number of nodes below first branch (1) | 31 |
| Number of cm. from crown to first branch (1) | 60.3 |
| Number of branches (1) | 54 |
| Number cm. between first and last branch (1) | 161.3 |
| Internode length in cm. between branches (1) | 2.99 |
| Number of cladophyll nodes beyond last branch (1) | 45 |
| Number of cm. beyond last branch (1) | 38.1 |
| Internode length in cm. beyond last branch (1) | 0.85 |
| Largest stalk in mm | 24.5 |
| Mean diameter of three largest stalks in mm | 24.4 |
| Number of stalks | 23 |
| Stalk vigor index number x mean diameter | 13,693 |
| Mature stalk color, bloom removed | 21–14 |
| Crown to first branch of highest headed stalk cm | 87.0 |
| Length of highest headed stalk cm | 235.0 |
| Flower data | |
| Petal tip (yellow) | 25–3 |
| Petal base (green) | 23–11 |
| Flower length mm | 4.2 |
| Flower width at midpoint mm | 2.4 |
| Fruit data (362M × 22–8) | |
| Weight of 100 fruit (g) | 30.8 |
| Water displacement of 100 fruit (ml) | 33.0 |
| Number of seed per 100 fruit | 399 |
| Weight of seed per 100 fruit (g) | 12.3 |
| Mean weight per seed | 0.0308 |
| Water displacement of seed of 100 fruit (ml) | 14.0 |
| Mature fruit color | 33–12 |
| Cladophyll data | |
| Number per node | 3.6 |
| Length (mm) | 17.6 |
| Width (mm) | 0.147 |

We claim:

1. A new and distinct Asparagus plant as herein shown and described, characterized particularly as to novelty by its tolerance to rust (*Puccinia asparagi*) and Fusarium infestation, and its vigor, together with high yield and tight spear tip formation for improved commercial table use.

* * * * *